United States Patent
Yuan et al.

(10) Patent No.: US 10,736,913 B1
(45) Date of Patent: Aug. 11, 2020

(54) USE OF INOSINE FOR CANCER IMMUNOTHERAPY

(71) Applicant: IMMUNOSPARKLE BIOSCIENCE LLC, Houston, TX (US)

(72) Inventors: Xiangliang Yuan, Manvel, TX (US); Baokun He, Pearland, TX (US)

(73) Assignee: IMMUNOSPARKLE BIOSCIENCE LLC, Houston, TX (US)

( * ) Notice: Subject to any disclaimer, the term of this patent is extended or adjusted under 35 U.S.C. 154(b) by 0 days.

(21) Appl. No.: 16/823,144

(22) Filed: Mar. 18, 2020

Related U.S. Application Data

(60) Provisional application No. 62/822,524, filed on Mar. 22, 2019.

(51) Int. Cl.
| | | |
|---|---|---|
| *A01N 43/04* | (2006.01) | |
| *A61K 31/70* | (2006.01) | |
| *A61K 31/708* | (2006.01) | |
| *A61K 31/522* | (2006.01) | |
| *C07K 16/28* | (2006.01) | |
| *A61K 9/00* | (2006.01) | |
| *A61K 45/06* | (2006.01) | |

(52) U.S. Cl.
CPC .......... *A61K 31/708* (2013.01); *A61K 31/522* (2013.01); *C07K 16/2818* (2013.01); *C07K 16/2827* (2013.01); *A61K 9/0019* (2013.01); *A61K 9/0053* (2013.01); *A61K 45/06* (2013.01)

(58) Field of Classification Search
None
See application file for complete search history.

(56) References Cited

PUBLICATIONS

He et al. Oncotarget (20117), vol. 8, pp. 67129-67139.*
Namdar A. et al. Iran J Immunol. (2015), vol. 12(3), pp. 176-187.*
Mahoney et al. Nature Reviews (2015), vol. 14, pp. 561-585.*
Costanzi, J. J., Coltman Jr, C. A., & Col, L. (1969). Combination chemotherapy using cyclophosphamide, vincristine, methotrexate and 5-fluorouracil in solid tumors. Cancer, 23(3), 589-596.*
Geary, S. M., Lemke, C. D., Lubaroff, D. M., & Salem, A. K. (2013). The combination of a low-dose chemotherapeutic agent, 5-fluorouracil, and an adenoviral tumor vaccine has a synergistic benefit on survival in a tumor model system. PloS one, 8(6).*
Fanciullino et al. Pharmaceutical Research (2005), vol. 22, pp. 2051-2057.*
Cory et al. Cancer Research (1979), vol. 39, pp. 4905-4913.*
Baggott, J. E., & Morgan, S. L. (2007). Methotrexate and erythro-9-(2-hydroxynon-3-yl) adenine therapy for rat adjuvant arthritis and the effect of methotrexate on in vivo purine metabolism. European journal of pharmaceutical sciences, 31(2), 95-101.*
Nuijen et al. Drug Development and Industrial Pharmacy (2001), vol. 27, pp. 767-780.*

\* cited by examiner

*Primary Examiner* — Patrick T Lewis
(74) *Attorney, Agent, or Firm* — Eric P. Mirabel

(57) ABSTRACT

Disclosed are formulations for the treatment of cancer including inosine or a related compound in combination with an immune checkpoint inhibitor including but not limited to immune checkpoint inhibitor binding agents (including anti-CTLA4, anti-PD1, anti-LAG-3, anti-TIM-3, anti-TIGIT, anti-CD47, anti-VISTA, and anti-PD-L1), and optionally also including a reinforcing agent to boost immune response, including CAR-T, CAR-NK, tumor vaccine, oncolytic virus vaccine, TLR7/8 agonist, anti-CD47 or IL-2 receptor agonist, and optionally also including other pharmacologically immune-boosting active agents.

16 Claims, 17 Drawing Sheets
(13 of 17 Drawing Sheet(s) Filed in Color)

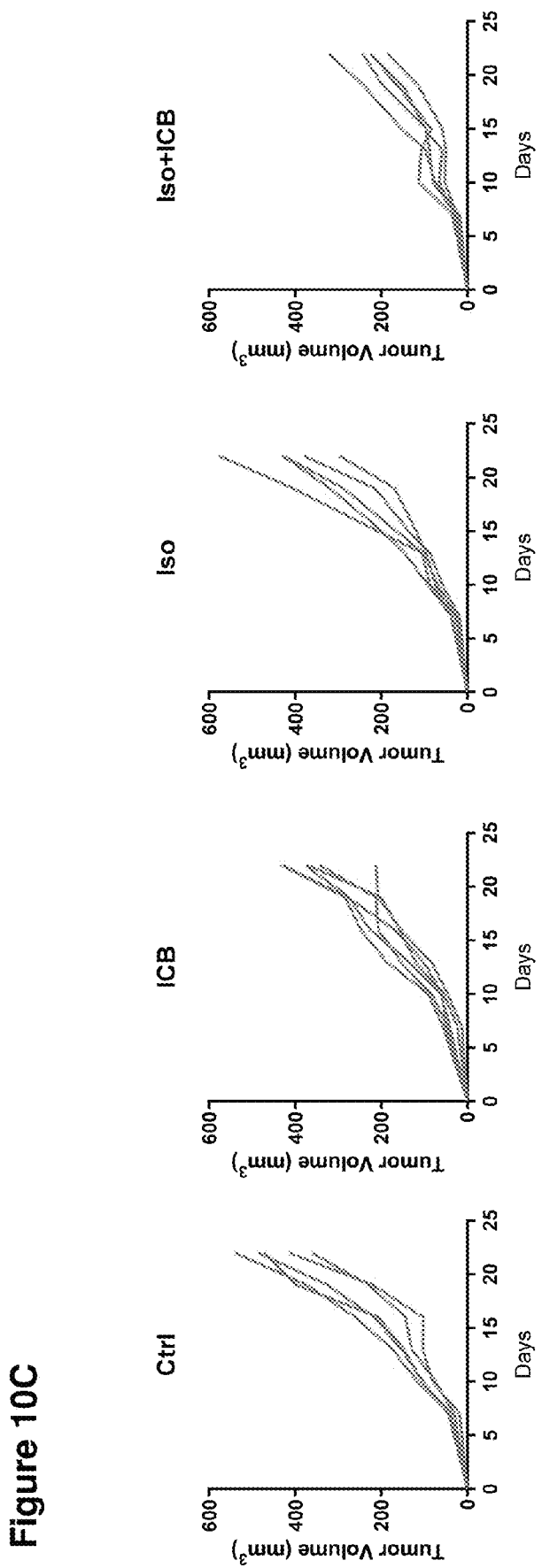

USE OF INOSINE FOR CANCER IMMUNOTHERAPY

BACKGROUND OF THE INVENTION

Novel immunotherapies, notably those acting on the immune checkpoint blockade (ICB), have been shown to be efficacious in patients with carcinoma (Ansel) et al., 2015; Carbone et al., 2017) and make remarkable progress in the clinical application. Immune checkpoint blockade (ICB) increases antitumor immunity by blocking native immune regulators such as the cytotoxic T lymphocyte antigen 4 (CTLA-4) and programmed cell death 1 antigen (PD-1) (Migden et al., 2018; Motzer et al., 2018; Tawbi et al., 2018).

Immune checkpoint blockade describes the use of therapeutic antibodies that disrupt negative immune regulatory checkpoints and unleash pre-existing antitumor immune responses. Such therapies block proteins called "checkpoints" that are made by certain immune system cells, such as T cells, and some cancer cells. These checkpoints help keep immune responses from being too strong and sometimes can keep T cells from killing cancer cells. When these checkpoints are blocked, T cells can kill cancer cells more effectively. Examples of checkpoint proteins found on T cells or cancer cells include PD-1/PD-L1 and CTLA-4/B7-1/B7-2. Checkpoint proteins, such as PD-L1 on tumor cells and PD-1 on T cells, help keep immune responses in check. The binding of PD-L1 to PD-1 keeps T cells from killing tumor cells in the body.

Blocking the binding of PD-L1 to PD-1 with an immune checkpoint inhibitor (e.g., anti-PD-L1 or anti-PD-1) allows the T cells to kill tumor cells. Checkpoint proteins, such as B7-1/B7-2 on antigen-presenting cells (APC) and CTLA-4 on T cells, help keep the body's immune responses in check. When the T-cell receptor (TCR) binds to the antigen and major histocompatibility complex (MHC) proteins on the APC and CD28 binds to B7-1/B7-2 on the APC, the T cell can be activated. However, the binding of B7-1/B7-2 to CTLA-4 keeps the T cells in the inactive state so they are not able to kill tumor cells in the body. Blocking the binding of B7-1/B7-2 to CTLA-4 with an immune checkpoint inhibitor (an anti-CTLA-4 antibody) allows the T cells to be activated and to kill tumor cells. Some immune checkpoint inhibitors are used to treat cancer.

However, current evidence indicates that single-agent immunotherapy is not effective for many patients. Innate or adaptive resistance has been observed with single-agent immunotherapy (Pitt et al., 2016; Sharma et al., 2017), underscoring the unmet need for effective, non-toxic combination treatment strategies that can improve efficacy in a broader patient population (George et al., 2018).

A number of emerging ("second-generation") therapies incorporate CTLA-4 and PD-1 checkpoint inhibitors as a "backbone" with other immunotherapies or non-immune based strategies in synergistic combination. These include targeted therapies such as tyrosine kinase inhibitors, co-stimulatory mAbs, epigenetic modulators, vaccines, adoptive T-cell therapy, and oncolytic viruses. A number of metabolic mechanisms, such as tryptophan, arginine and purine metabolism, have also been shown to be essential for immune evasion of tumors and could serve as co-targets in immunotherapy. Among purine metabolism, purine nucleosides, such as adenosine and its primary metabolite inosine, are low molecular weight molecules that participate in a wide variety of intracellular biochemical processes. Adenosine has a short half-life (approximately 10 seconds) and is rapidly deaminated to inosine, a stable metabolite with a half-life of approximately 15 h. Events such as inflammation, hypoxia, and tissue injury have been thought to account for adenosine degradation and generation of its metabolite inosine.

Inosine is a common component of food and was previously believed to be an inactive breakdown product and, unlike adenosine, little attention has been paid to its physiological role. However, recent studies demonstrate that inosine has neuroprotective, cardioprotective and immunomodulatory effects (Hasko et al., 2004). Also, it has been recognized that adenosine can bind to adenosine receptors and initiate intracellular signaling. Adenosine acting through adenosine receptors (ARs) exerts a wide range of anti-inflammatory and immunomodulatory effects in vivo (Hasko et al., 2004). Moreover, previous studies show that inosine produces anti-inflammatory effects related to the activation of adenosine receptors, mainly the A2a and A3 receptor whose activation can contribute to the reduction of pro-inflammatory cytokines, and tissue protective effects from endotoxin-induced and 2,4,6-trinitrobenzene sulfonic acid (TNBS)-induced inflammation. However, some studies demonstrate that inosine can't be used as an adenosine receptor agonist.

The immunomodulatory effects of inosine in vivo cannot be explained fully by in vitro pharmacological characterization of inosine at the A2AR (Welihinda et al., 2016). Notably, the potential function of inosine on tumor cells has not been fully elaborated. The effect of inosine on the efficacy of immune checkpoint blockades or other pharmacologically immune active agents remains unclear. Given the in vivo stability of inosine, it was previously unrecognized that inosine can amplify the anti-tumor efficacy of ICB in vivo.

SUMMARY OF THE INVENTION

The present invention relates to formulations for the treatment of cancer including inosine or a related compound in combination with an immune checkpoint inhibitor (a blocking agent to immune cells inhibitory receptor) including but not limited to immune checkpoint inhibitor antibodies and proteins (including anti-CTLA4, anti-PD1, anti-PD-L1, anti-B7-1 and anti-B7-2, anti-LAG-3, anti-TIM-3, anti-TIGIT and anti-VISTA.), and optionally also including a reinforcing agent to boost immune response, including CAR-T, CAR-NK, tumor vaccine, oncolytic virus vaccine, TLR7/8 agonist, anti-CD47 or IL-2 receptor agonist, and optionally also including other pharmacologically immune active agents. Commercially available anti-PD1 antibodies include nivolumab, pembrolizumab, Cemiplimab, Toripalimab, Sintilimab, Camrelizumab, Tislelizumab. Commercially available PD-L1 inhibitors include atezolizumab, avelumab, durvalumab. Commercially available CTLA4 inhibitors include ipilimumab. All such antibodies and proteins (collectively encompassed in the term "Binding Agents" described below), and combinations thereof, are suitable for use in the formulations of the invention.

The invention relates to the finding that inosine and related compounds can strongly sensitize tumor cells to the cytolytic effect of immune cells by enhancing tumor immunogenicity. Based on this, inosine and related compounds cooperate with immune checkpoint inhibitors and activate anti-tumor immune responses in the presence of the tumor. Inosine (and related compounds) can act with immune checkpoint inhibitors in the treatment of mammalian cancer or tumors which are sensitive or resistive to immune checkpoint inhibitors alone, or which are resistant to conventional immunotherapy.

The invention includes: treating cancer or tumors which are sensitive or resistive to immune checkpoint inhibitors by administrating an effective amount of inosine, or a related compound to inosine.

Compounds related to inosine which are expected to function in the same treatment role, and in the same compositions and formulations, including in combination therapies, include purine nucleosides which have a similar structure to inosine (IUPAC name: 9-[(2R,3R,4S,5R)-3,4-dihydroxy-5-(hydroxymethyl)oxolan-2-yl]-1H-purin-6-one, having the structure:

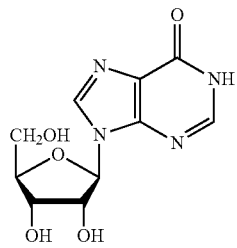

Such compounds with a similar structure which would be expected to be effective, include all compounds with any different alcohol than the hydroxymethyl group above, including alcohols where the methyl in the hydroxymethyl group is substituted by an alkane, alkene or alkyne, branched or unbranched, having two or more carbon atoms in the chain. Such compounds with a similar structure further include hypoxanthine, xanthine, hydroxyl-deoxyguanosine, 2',3'-Dideoxyinosine, 2'-Deoxyinosine, inosinic acid, inosine diphosphate, inosine triphosphate, sodium inosinate, isoprinosine, deoxyinosine, 3'-Deoxy-3'-fluoroinosine, 1-Methylinosine, Inosine 5'-methyl monophosphate, and inosine-3',5'-Cyclic Monophosphate. Administering one or more of such compounds to enhance immune response and augment the potency of immune checkpoint inhibitors or other pharmacologically immune-boosting active agents is also within the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

µg per mouse) and anti-PD-1 antibody (200 µg per mouse) were injected i.p on days 7, 10, 13 and 16. 400 mg/kg of inosine per day was orally administered to mice from day 4 to day 21. Results show that the combination of inosine and ICB treatment significantly reduce the regression of B16-GM tumor in tumor-bearing mice compared to the control group, or only inosine or ICB treatment.

Figure 4A:
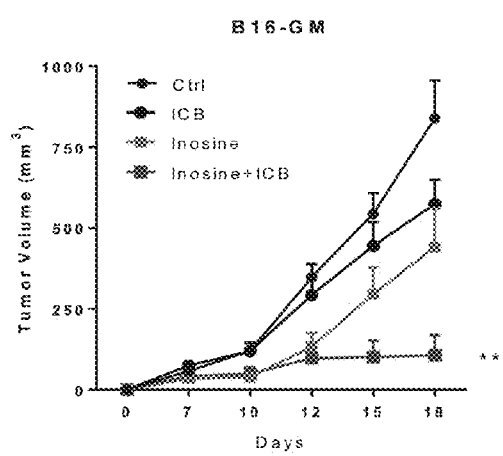
FIG. 4A shows the tumor volume (mm$^3$, y-axis) over time after B16-GM tumor cell challenge (x-axis) in mice treated with control vehicle, inosine, ICB (anti-CTLA4 Ab and anti-PD-1 Ab), or inosine and anti-ICB. B16-GM cells were injected subcutaneously into eight-week-old female C57BL/6 mice (2×10$^5$/mouse). Anti-CTLA4 antibody (100
Figure 4B:
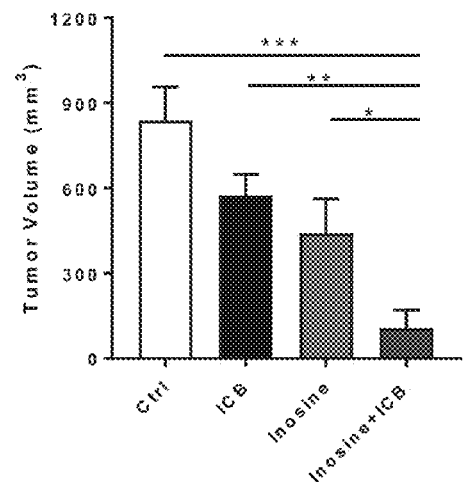

FIG. 4B shows the average tumor volumes ($mm^3$) on day 18 after challenging mice with B16-GM tumor cells with the indicated treatment (as in FIG. 4A). These results indicate that the combination of inosine and ICB treatment is superior to inosine or ICB treatment, alone (wherein * P<0.05;  P<0.01;  P<0.001) in inhibiting tumor progression.

Figure 4C:
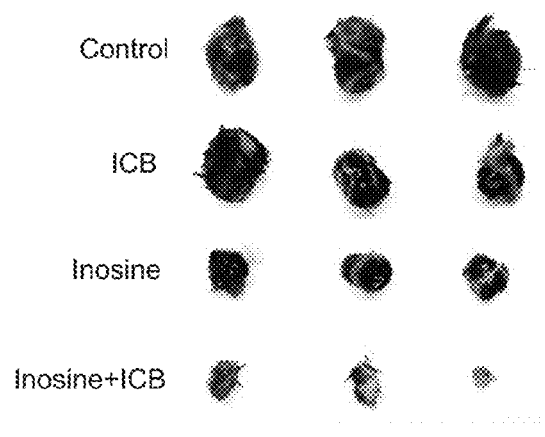

FIG. 4C depicts the images of endpoint B16-GM tumors for each group, treated as in FIG. 4A. The results show smaller tumors in mice in the Inosine+ICB treatment group than in other groups.

Figure 4D:
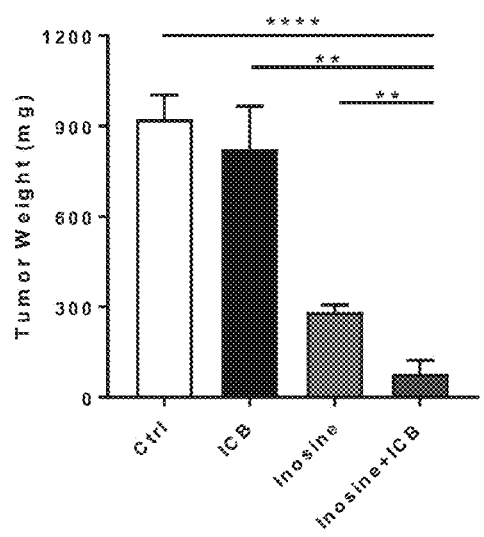

FIG. 4D depicts the endpoint tumor weight in grams (mice treated as in FIG. 4A), showing a significant reduction in B16-GM tumor size where a combination of inosine with anti-CTLA4 antibody and anti-PD1 antibody ("ICB") immunotherapy was used. Results are shown as mean±SEM ( P<0.01; ** P<0.0001). Tumor weight statistics were calculated using the unpaired t-test with Welch's correction.

Figure 5:
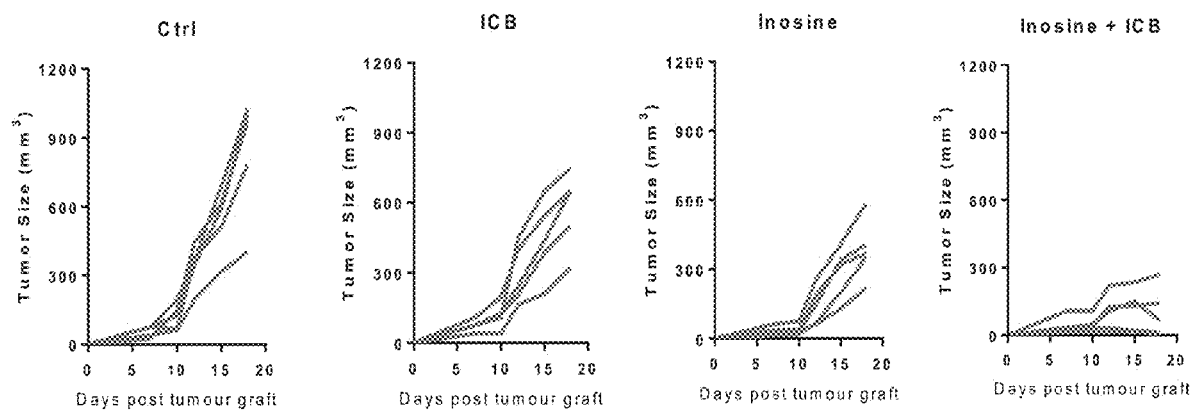

FIG. 5 shows the individual tumor growth curves of each treatment group of B16-GM tumor-bearing mice, treated with Ctrl, inosine, anti-CTLA4 antibody and anti-PD1 antibody ("ICB") or Inosine+ICB treatment. The results demonstrate that Inosine+ICB treatment is more efficacious than inosine or ICB treatment, alone, in inhibiting tumor growth. Notably, tumors in two of five mice are completely inhibited by Inosine+ICB treatment.

Figure 6A:
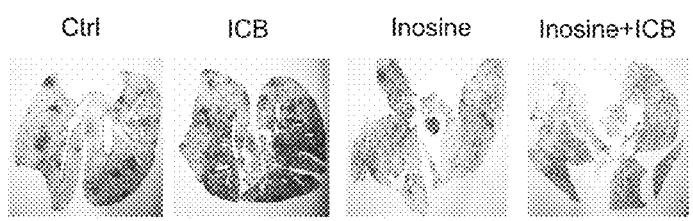

FIG. 6A shows the representative H&E (hematoxylin and eosin) stained sections of the lung from B16-GM tumor-bearing mice at day 18 treated with control vehicle, inosine, anti-CTLA4 antibody and anti-PD1 antibody ("ICB"), or inosine+ICB.

Figure 6B:
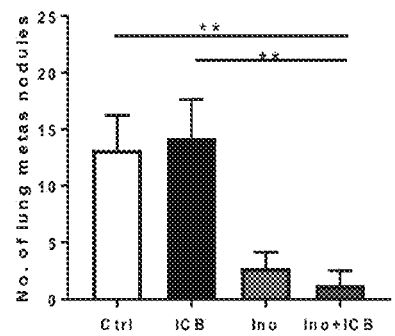

FIG. 6B shows the quantification of lung metastasis at day 18 from a B16-GM tumor challenge, as in FIG. 6A. These indicate that inosine and ICB combination treatment significantly inhibits the metastasis of lung B16-GM tumors compared to control vehicle or inosine or ICB alone. Lung metastatic nodules statistics were calculated using the unpaired t-test with Welch's correction. Results are shown as mean±SEM (** P<0.01).

Figure 7:
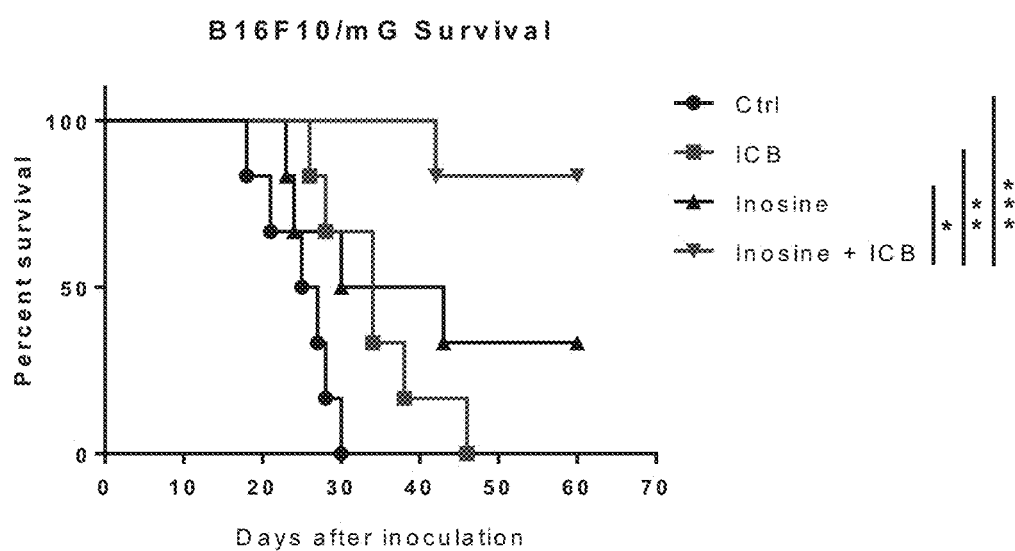

FIG. 7 shows the survival curves of B16-GM tumor-bearing mice that were treated control, inosine, anti-CTLA4 antibody and anti-PD1 antibody ("ICB"), or Inosine+ICB. For the survival curves, a mouse was considered dead when the tumor volume reached 2500 $mm^3$. These results indicate that Inosine+ICB treatment significantly prolongs the survival of B16-GM tumor-bearing mice compared with inosine or ICB treatment, alone. Survival statistics were calculated using the Log-rank (Mantel-Cox) test (wherein * P<0.05;  P<0.01; * P<0.001).

Figure 8A:
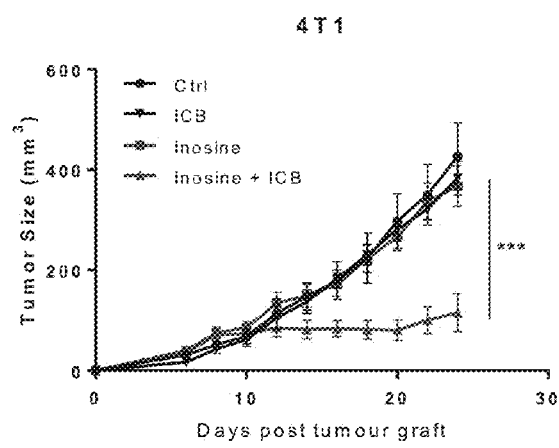

FIG. 8A shows the average tumor volume ($mm^3$, y-axis) over time after 4T1 breast cancer cell challenge (x-axis) in mice treated with control vehicle, inosine, anti-CTLA4 antibody and anti-PD1 antibody ("ICB"), or inosine+ICB. 4T1 cells were injected into the mammary fat pad of eight-week-old female Balb/c mice ($2\times10^5$/mouse). Anti-CTLA4 antibody (100 µg per mouse) and anti-PD-1 antibody (200 µg per mouse) were injected i.p on days 7, 10, 13 and 16. 400 mg/kg body weight of inosine per day was orally administered to mice from day 4 until day 21. The results show that the combination of inosine and ICB notably inhibits tumor progression in 4T1 tumor-bearing mice in comparison to the control group or cohorts treated with inosine or ICB alone. Results are shown as mean±SEM. (*** indicates P<0.001).

Figure 8B:
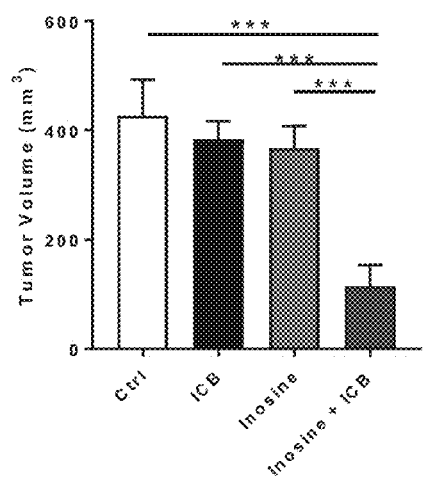

FIG. 8B shows the average tumor volumes ($mm^3$) on day 24 for mice bearing 4T1 tumor cells, challenged with the indicated treatment, as in FIG. 8A. These results indicate that the combination of inosine and ICB treatment inhibits tumor growth in 4T1 tumor-bearing mice, but that inosine or ICB alone does not significantly affect tumor growth. Tumor volume statistics were calculated using the unpaired t-test with Welch's correction (***P<0.001).

Figure 8C:
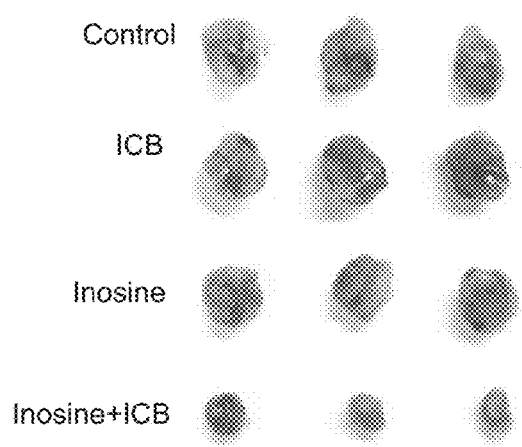

FIG. 8C depicts the representative images of end-point 4T1 tumors for each group, treated as in FIG. 8A, and showing smaller tumor size in mice treated with the combination of inosine and ICB, compared to other groups.

Figure 8D:
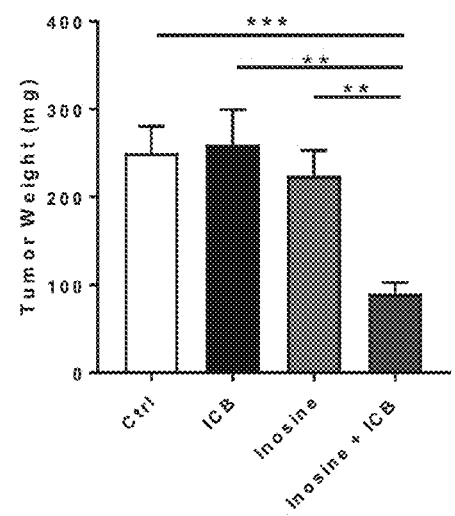

FIG. 8D, treated as in FIG. 8A where the end-point tumor weight is in grams, shows a significant reduction in 4T1 tumor size using a combination of inosine and ICB immunotherapy. Tumor weight statistics were calculated using the unpaired t-test with Welch's correction. Results are shown as mean±SEM ( P<0.01; * P<0.001).

Figure 9:
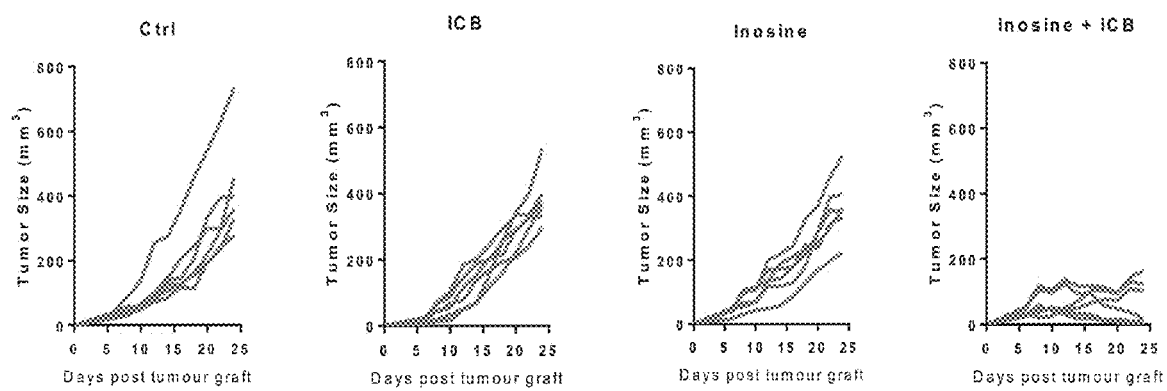

FIG. 9 shows the individual tumor growth curves of each treatment group of mice challenged with 4T1 tumor cells as in FIG. 8A, that were treated with control, inosine, anti-CTLA4 antibody and anti-PD1 antibody ("ICB") or Inosine+ICB. The results demonstrate that Inosine+ICB treatment is more efficacious in treating 4T1 tumors than inosine or ICB treatment, alone. Notably, the growth of three of six tumors (50%) is completely inhibited by the combination of Inosine+ICB treatment.

Figure 10B:
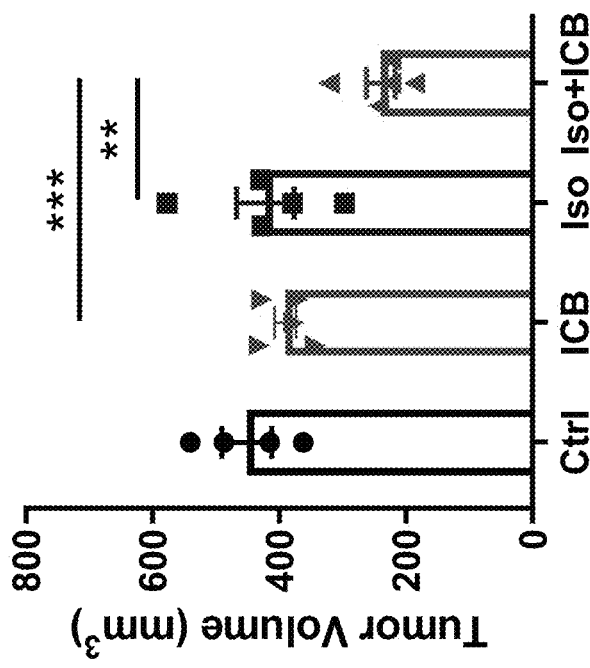
Figure 10A:
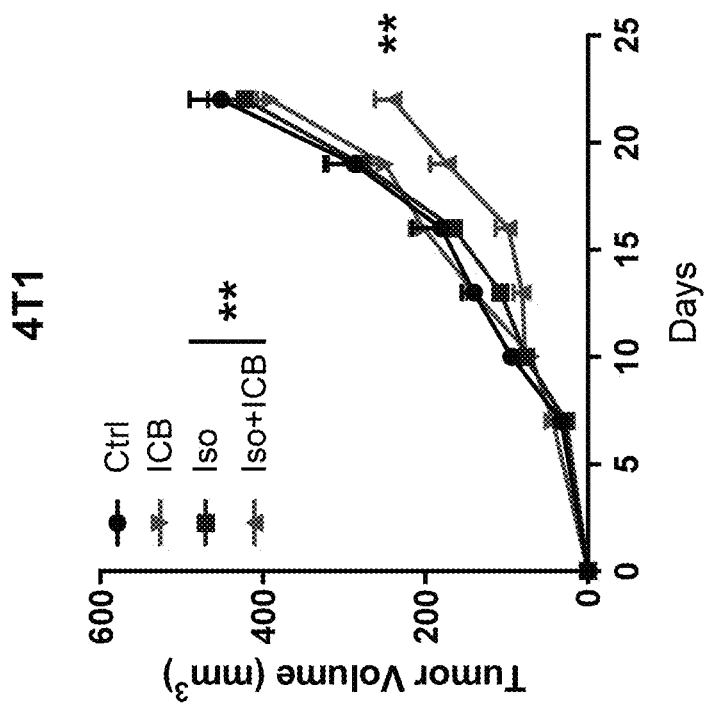

FIG. 10A shows average tumor volume ($mm^3$, y-axis) over time after 4T1 breast cancer cell challenge (x-axis) in mice treated with control vehicle, Isoprinosine (Iso), with anti-CTLA4 antibody and anti-PD1 antibody ("ICB"), or Isoprinosine and ICB. 4T1 cells were injected into the mammary fat pad of eight-week-old female Balb/c mice ($2\times10^5$/mouse). Anti-CTLA4 antibody (100 µg per mouse) and anti-PD-1 antibody (200 µg per mouse) were injected i.p on days 7, 10, 13 and 16. 400 mg/kg body weight of Isoprinosine (Iso) per day was orally administered to mice from day 5 until day 20. The results show that the combination of Isoprinosine (Iso) and ICB have a dramatic effect on tumor regression in 4T1 tumor-bearing mice in comparison to the control group or cohorts treated with Isoprinosine or ICB alone. Results are shown as mean±SEM. (** indicates P<0.01)

FIG. 10B shows the average tumor volumes ($mm^3$) on day 22 after 4T1 tumor cell challenge in mice as in FIG. 10A. These results indicate that the combination of Isoprinosine (Iso) and ICB treatment likely have a synergistic effect in reducing tumor growth in 4T1 tumor-challenged mice. Tumor volume statistics were calculated using the unpaired t-test with Welch's correction ((*P<0.05; **P<0.01).

FIG. 10C shows the individual tumor growth curves of each treatment group of 4T1 in mice that were treated with control, Isoprinosine (Iso), ICB, or Iso+ICB as in FIG. 10A. The results demonstrate that the efficacy of Isoprinosine+ICB treatment in 4T1 tumors is superior to Isoprinosine alone or ICB treatment alone, respectively.

DETAILED DESCRIPTION

It should be understood that unless the context clearly dictates otherwise, the singular forms "a", "an" and "the" include plural forms. The terms "Binding Agent" include antibodies and derivatives of antibodies, described below, as well as proteins and other molecules which bind the same target(s) as antibodies described herein.

The results described above show that inosine enhances the anti-tumor effects of immune checkpoint inhibitors (aka "ICB" for "immune checkpoint blockade"), including antibodies to immune checkpoint molecules such as PD-1, CTLA-4, LAG-3, TIM-3, TIGIT and VISTA. The invention includes inosine and related compounds in combination with Binding Agents targeting CTLA-4, PD-1 or PD-L1, LAG-3, TIM-3, TIGIT and VISTA, administered for tumor or cancer treatment.

Typically, an antibody has a heavy and light chain. Each heavy and light chain contains a constant region and a variable region (VH and VL, respectively). The regions are also known as "domains." Light and heavy chain variable regions contain a "framework" region interrupted by three hypervariable regions, also called "complementarity-determining regions" or "CDRs." The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found.

In one preferred embodiment, an anti-CTLA-4, anti-PD-1 or anti-PD-L1 monoclonal antibody (usually generated in mice or other rodents) or a fragment thereof is a chimeric, humanized, or human antibody. Generally, a humanized antibody has one or more amino acid residues introduced into it from a source that is non-human. These non-human amino acid residues are often referred to as import residues, which are typically taken from an import variable domain. Humanization can be essentially performed following the methods described in Jones et al., Nature 321: 522-525 (1986); Riechmann et al., Nature 332: 323-327 (1988); or Verhoeyen et al., Science 239: 1534-1536 (1988), by substituting rodent CDRs or CDR sequences for the corresponding sequences of a human antibody. Accordingly, such humanized antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

In some embodiments, "human antibody" refers to an immunoglobulin comprising human hypervariable regions in addition to human framework and constant regions. Such antibodies can be produced using various techniques known in the art. For example in vitro methods involve use of recombinant libraries of human antibody fragments displayed on bacteriophage (e.g., McCafferty et al, 1990, Nature 348: 552-554; Hoogenboom &Winter, J. Mol. Biol. 227: 381 (1991); and Marks et al, J. Mol. Biol. 222: 581 (1991)), yeast cells (Boder and Wittrup, 1997, Nat Biotechnol 15: 553-557), or ribosomes (Hanes and Pluckthun, 1997, Proc Natl Acad Sci USA 94: 4937-4942). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 6,150,584; 5,545,807; 5,545,806; 5,569,825; 5,625,126; 5,633,425; 5,661,016, and in the following scientific publications: (e.g., Jakobavits, Drug Deliv Rev. 31: 33-42 (1998), Marks et al, Bio/Technology 10: 779-783 (1992); Lonberg et al, Nature 368: 856-859 (1994); Morrison, Nature 368: 812-13 (1994); Fishwild et al, Nature Biotechnology 14: 845-51 (1996); Neuberger, Nature Biotechnology 14: 826 (1996); Lonberg & Huszar, Intern. Rev. Immunol. 13: 65-93 (1995).

In certain embodiments, the antibody or the fragment thereof disclosed herein comprises or is an F(ab)'2, an Fab, an Fv, or a single-chain Fv fragment of the above ICB antibodies.

In some embodiments, "antibody fragments" means molecules that comprise a portion of an intact antibody, generally the antigen binding or variable region of the intact antibody. Examples of antibody fragments include Fab, Fab', F(ab)'2, and Fv fragments; single domain antibodies (see, e.g., Wesolowski, Med Microbiol Immunol. (2009) 198 (3): 157-74; Saerens, et al., Curr Opin Pharmacol. (2008) 8 (5): 600-8; Harmsen and de Haard, Appl Microbiol Biotechnol. (2007) 77 (1): 13-22)); helix-stabilized antibodies (see, e.g., Arndt et al., J Mol Biol 312: 221-228 (2001); diabodies (see below); single-chain antibody molecules ("scFvs," see, e.g., U.S. Pat. No. 5,888,773); disulfide stabilized antibodies ("dsFvs", see, e.g., U.S. Pat. Nos. 5,747,654 and 6,558,672), and domain antibodies ("dAbs," see, e.g., Holt et al., Trends Biotech 21 (11): 484-490 (2003), Ghahroudi et al., FEBS Lett. 414: 521-526 (1997), Lauwereys et al., EMBO J 17: 3512-3520 (1998), Reiter et al., J. Mol. Biol. 290: 685-698 (1999), Davies and Riechmann, Biotechnology, 13: 475-479 (2001)).

U.S. Pat. No. 5,932,448, discloses making of bispecific antibodies with Fab' portions joined by a leucine zipper; U.S. Pat. No. 7,538,196, discloses making of bispecific antibodies where portions are joined with a linker; U.S. Pat. No. 8,148,496 discloses a multi-specific Fv antibody construct having at least four variable domains which are linked with each other via peptide linkers. A bispecific antibody could have one arm targeting ICB and the other arm targeting a tumor or cancer marker.

US Publ'n No. 20170335281 describes making of a genetically modified T cell expressing a CAR that comprises an antigen binding domain that binds to a cancer associated antigen. The same general techniques can be applied to modify T cells or other immune effector cells to express one or more of CDR1, CDR2 and CDR3 of an antigen binding domain, for cancer treatment. The antigen binding domain of the CAR polypeptide molecule can include any antibody, antibody fragment, an scFv, a Fv, a Fab, a (Fab')$_2$, a single domain antibody (SDAB, disclosed in WO 9404678 and Hamers-Casterman, C. et al. (1993) Nature 363:446-448), a VH or VL domain, or a VHH domain. Such CAR expressing T cells could be used in combination with the therapy described herein, or the antigen binding domain could be an ICB domain.

High Affinity Antibody Variants

Making of ICB antibodies with high affinity is set forth below.

Antibodies should be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved.

Examples of framework region residues to modify include those which non-covalently bind target directly (Amit et al. Science 233: 747-753 (1986)); interact with/effect the conformation of CDR (Chothia et al. J. Mol. Biol. 196: 901-917 (1987)); and/or participate in the VL-VH interface (EP 239 400 B1). In certain embodiments, modification of one or more of such framework region residues results in an enhancement of the binding affinity of the antibody for the target of interest.

Nucleic acid molecules encoding amino acid sequence variants are prepared by a variety of methods known in the art. These methods include, but are not limited to, oligonucleotide-mediated (or site-directed) mutagenesis, PCR mutagenesis, and cassette mutagenesis of an earlier prepared variant or a non-variant version of the species-dependent antibody. The preferred method for generating variants is an oligonucleotide-mediated synthesis. In certain embodiments, the antibody variant will only have a single hypervariable region residue substituted, e.g. from about two to about fifteen hypervariable region substitutions.

One method for generating the library of variants is by oligonucleotide mediated synthesis. Three oligonucleotides of approximately 100 nucleotides each may be synthesized spanning the entire light chain or heavy chain variable region. Each oligonucleotide may comprise: (1) a 60 amino acid stretch generated by the triplet $(NNK)_{20}$ where N is any nucleotide and K is G or T, and (2) an approximately 15-30 nucleotide overlap with either the next oligo or with the vector sequence at each end. Upon annealing of these three oligonucleotides in a PCR reaction, the polymerase will fill in the opposite strand generating a complete double stranded heavy chain or light chain variable region sequence. The number of triplets may be adjusted to any length of repeats and their position within the oligonucleotide may be chosen so as to only substitute amino acids in a given CDR or framework region. By using (NNK), all twenty amino acids are possible at each position in the encoded variants. The overlapping sequence of 5-10 amino acids (15-30 nucleotides) will not be substituted, but this may be chosen to fall within the stacking regions of the framework, or may substituted by a separate or subsequent round of synthesis. Methods for synthesizing oligonucleotides are well known in the art and are also commercially available. Methods for generating the antibody variants from these oligonucleotides are also well known in the art, e.g., PCR.

The library of heavy and light chain variants, differing at random positions in their sequence, can be constructed in any expression vector, such as a bacteriophage, each of which contains DNA encoding a particular heavy and light chain variant.

Following production of the antibody variants, the biological activity of variant relative to the parent antibody is determined. As noted above, this involves determining the binding affinity of the variant for the ICB target. Numerous high-throughput methods exist for rapidly screen antibody variants for their ability to bind the target of interest.

One or more of the antibody variants selected from this initial screen may then be screened for enhanced binding affinity relative to the parent antibody. One common method for determining binding affinity is by assessing the association and dissociation rate constants using a BIAcore surface plasmon resonance system (BIAcore, Inc.). A biosensor chip is activated for covalent coupling of the target according to the manufacturer's (BIAcore) instructions. The target is then diluted and injected over the chip to obtain a signal in response units (RU) of immobilized material. Since the signal in RU is proportional to the mass of immobilized material, this represents a range of immobilized target densities on the matrix. Dissociation data are fit to a one-site model to obtain koff+/−s.d. (standard deviation of measurements). Pseudo-first order rate constant (ks) are calculated for each association curve, and plotted as a function of protein concentration to obtain kon+/−s.e. (standard error of fit). Equilibrium dissociation constants for binding, Kd's, are calculated from SPR measurements as koff/kon. Since the equilibrium dissociation constant, Kd, is inversely proportional to koff, an estimate of affinity improvement can be made assuming the association rate (kon) is a constant for all variants.

The resulting candidate(s) with high affinity may optionally be subjected to one or more further biological activity assays to confirm that the antibody variant(s) with enhanced binding affinity still retain the desired therapeutic attributes, as can be tested in the assays described in the figures above. The optimal antibody variant retains the ability to bind the ICB target with a binding affinity significantly higher than the parent antibody.

The antibody variant(s) so selected may be subjected to further modifications oftentimes depending upon the intended use of the antibody. Such modifications may involve further alteration of the amino acid sequence, fusion to heterologous polypeptide(s) and/or covalent modifications such as those elaborated below. For example, any cysteine residues not involved in maintaining the proper conformation of the antibody variant may be substituted, generally with serine, to improve the oxidative stability of the molecule and prevent aberrant cross linking. Conversely, (a) cysteine bond(s) may be added to the antibody to improve its stability (particularly where the antibody is an antibody fragment such as an Fv fragment).

"Binding Agents" refers to all antibodies and fragments or derivatives of antibodies as described above, as well as proteins and molecules other than antibodies and fragments or derivatives of antibodies which target immune checkpoint blockade proteins or can inhibit the immune checkpoint blockade, any of which could be modified and tested to become Binding Agents with high affinity for ICBs, using techniques similar to those described above.

Formulations

After preparation of a suitable Binding Agent, it can be prepared in a formulation for administration to a subject, in combination with inosine or the inosine-related compound. A lyophilized formulation is preferred for the Binding Agent, which as a first step, requires preparing a pre-lyophilized formulation. The amount of Binding Agent in the pre-lyophilized formulation is determined taking into account the desired dose volumes, mode(s) of administration etc. The Binding Agent is generally present in solution. For example, the Binding Agent may be present in a pH-buffered solution at a pH from o about 4-8, and preferably from about 5-7. Exemplary buffers include histidine, phosphate, Tris, citrate, succinate and other organic acids. The buffer concentration can be from about 1 mM to about 20 mM, or from about 3 mM to about 15 mM, depending, for example, on the buffer and the desired isotonicity of the formulation (e.g. of the reconstituted formulation). The preferred buffer is histidine as it can have lyoprotective properties. Succinate is also a useful buffer.

The lyoprotectant is added to the pre-lyophilized formulation. In preferred embodiments, the lyoprotectant is a non-reducing sugar such as sucrose or trehalose. The amount of lyoprotectant in the pre-lyophilized formulation is generally such that, upon reconstitution, the resulting formulation will be isotonic, as preferred, though hypertonic reconstituted formulations may also be suitable. In addition, the amount of lyoprotectant must not be too low such that an unacceptable amount of degradation/aggregation of the Binding Agent occurs upon lyophilization.

Where the lyoprotectant is a sugar (such as sucrose or trehalose) and the Binding Agent is an antibody, exemplary lyoprotectant concentrations in the pre-lyophilized formulation are from about 10 mM to about 400 mM, and preferably from about 30 mM to 5 about 300 mM, and most preferably from about 50 mM to about 100 mM.

The ratio of Binding Agent to lyoprotectant is selected for each Binding Agent and lyoprotectant combination. In the case of an antibody as the Binding Agent and a sugar (e.g., sucrose or trehalose) as the lyoprotectant for generating an isotonic reconstituted formulation with a high protein concentration, the molar ratio of lyoprotectant to antibody may be from about 100 to about 1500 moles lyoprotectant to 1 mole antibody, and preferably from about 200 to about 1000 moles of lyoprotectant to 1 mole antibody, including from about 200 to about 600 moles of lyoprotectant to 1 mole antibody.

In preferred embodiments, it has been found to be desirable to add a surfactant to the pre-lyophilized formulation. Alternatively, or in addition, the surfactant may be added to the lyophilized formulation and/or the reconstituted formulation. Exemplary surfactants include nonionic surfactants such as polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palnidopropyl-, or isostearamidopropyl-betaine (e.g lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), polyethyl glycol, polypropyl glycol, and copolymers of ethylene and propylene glycol (e.g. Pluronics, PF68 etc). The amount of surfactant added is such that it reduces aggregation of the reconstituted protein and minimizes the formation of particulates after reconstitution. For example, the surfactant may be present in the pre-lyophilized formulation in an amount from about 0.001-0.5%, and preferably from about 0.005-0.05%.

A mixture of the lyoprotectant (such as sucrose or trehalose) and a bulking agent (e.g. mannitol or glycine) may be used in the preparation of the pre-lyophilized formulation. The bulking agent may allow for the production of a uniform lyophilized cake without excessive pockets therein.

Other pharmaceutically acceptable carriers, excipients or stabilizers such as those described in Remington's Pharmaceutical Sciences 16th edition, Osol, A. Ed. (1980) may be included in the pre-lyophilized formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include; additional buffering agents; preservatives; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The pharmaceutical compositions and formulations described herein are preferably stable, so as to retain its physical and chemical stability and integrity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be measured at a selected temperature for a selected time period.

The formulations to be used for in vivo administration must be sterile. This is readily accomplished by filtration through sterile filtration membranes, prior to, or following, lyophilization and reconstitution. Alternatively, sterility of the entire mixture may be accomplished by autoclaving the ingredients, except for protein, at about 120° C. for about 30 minutes.

After the Binding Agent, lyoprotectant and inosine (or related compound(s)) are mixed together, the formulation is lyophilized. Many different freeze-dryers are available for this purpose such as Hu1150® (Hull, USA) or GT20® (Leybold-Heraeus, Germany) freeze-dryers. Freeze-drying is accomplished by freezing the formulation and subsequently subliming ice from the frozen content at a temperature suitable for primary drying. Under this condition, the product temperature is below the eutectic point or the collapse temperature of the formulation.

Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will mainly dictate the time required for drying, which can range from a few hours to several days (e.g. 40-60 hrs). A secondary drying stage may be carried out at about 0-40° C., depending primarily on the type and size of container and the type of protein employed. For example, the shelf temperature throughout the entire water removal phase of lyophilization may be from about 15-30° C. (e.g., about 20° C.). The time and pressure required for secondary drying will be that which produces a suitable lyophilized cake, dependent, e.g., on the temperature and other parameters. The secondary drying time is dictated by the desired residual moisture level in the product and typically takes at least about 5 hours (e.g. 10-15 hours). The pressure may be the same as that employed during the primary drying step. Freeze-drying conditions can be varied depending on the formulation and vial size.

In some instances, it may be desirable to lyophilize the protein formulation in the container in which reconstitution of the protein is to be carried out in order to avoid a transfer step. The container in this instance may, for example, be a 3, 5, 10, 20, 50 or 100 cc vial. As a general proposition, lyophilization will result in a lyophilized formulation in which the moisture content thereof is less than about 5%, and preferably less than about 3%.

At the desired stage, typically when it is time to administer the formulation to the patient, the lyophilized formulation may be reconstituted with a diluent such that the Binding Agent concentration in the reconstituted formulation is preferably similar to that of the pre-lyophilized formulation.

Reconstitution generally takes place at a temperature of about 25° C. to ensure complete hydration, although other temperatures may be employed as desired. The time required for reconstitution will depend, e.g., on the type of diluent, amount of excipient(s) and protein. Exemplary diluents include sterile water, bacteriostatic water for injection (BWFI), a pH buffered solution (e.g. phosphate-buffered saline), sterile saline solution, Ringer's solution or dextrose solution. The diluent optionally contains a preservative. Exemplary preservatives have been described above, with aromatic alcohols such as benzyl or phenol alcohol being the preferred preservatives. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0% and preferably from about 0.5-1.5%, but most preferably about 1.0-1.2%.

Alternatively, a non-lyophilized formulation may be used, including a Binding Agent, inosine or a related compound, and any of the well-known carriers, excipients, buffers, stabilizers, preservatives, adjuvants and other additives described herein and well known in the art.

Dosages and Administration

The formulation described above can be administered to a subject (e.g., a human) in need of the treatment via a suitable route, such as administration by intravenous, intramuscular, intraperitoneal, intracerebrospinal, subcutaneous, intracutaneous, intraarticular, intrasynovial, intrathecal, intradermal, intratumoral, intranodal, intramedulla, oral, inhalation or topical routes; or it may be administered orally, by inhalation spray, topically, rectally, nasally, buccally, vaginally or via an implanted reservoir; and in any case, as a bolus or by continuous infusion over a period of time; or via injectable depot routes of administration such as using 1-, 3-, or 6-month depot injectable or biodegradable materials and methods.

Commercially available nebulizers for liquid formulations, including jet nebulizers and ultrasonic nebulizers are useful for administration. Liquid formulations can be directly nebulized and lyophilized powder can be nebulized after reconstitution. Alternatively, antibodies can be aerosolized using a fluorocarbon formulation and a metered dose inhaler, or inhaled as a lyophilized and milled powder. Where CAR is deployed in the invention, compositions of immune effector cells (e.g., T cells, NK cells) may be injected directly into a tumor, lymph node, or site of infection, or elsewhere.

The subject to be treated by the methods described herein can be a mammal, more preferably a human. Mammals include, but are not limited to, farm animals, sport animals, pets, primates, horses, dogs, cats, mice, and rats.

An "effective amount" refers to the amount of active agent required to confer therapeutic effect on the subject, either alone or in combination with one or more other active agents. Effective amounts vary, depending on the particular condition being treated, the severity of the condition, the individual patient parameters including age, physical condition, size, gender and weight, the duration of the treatment, the nature of concurrent therapy (if any), the specific route of administration and like factors, all of which are well known to those of ordinary skill in the art and can be addressed with no more than routine experimentation. It is generally preferred that a maximum dose of the individual components or combinations thereof be used, that is, the highest safe dose according to sound medical judgment. A lower dose or tolerable dose for medical reasons, psychological reasons or other reasons, is also appropriate.

Empirical considerations, such as the antibody half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of gastric cancer. Alternatively, sustained continuous release formulations of antibody may be appropriate. Various formulations and devices for achieving sustained release are known in the art.

In one example, dosages for the Binding Agent and inosine or related compounds, as described herein, may be determined empirically in individuals who have been given one or more administration(s) of the formulation. Individuals are given incremental dosages of the formulation. To assess the efficacy of the formulation, an indicator of the disease (e.g., tumor growth) can be followed according to routine practice.

Generally, for the administration of any of the formulation described herein, an initial candidate dosage can be extrapolated from the experiments described above. based on factors including, for example, age and weight of an individual, the condition requiring treatment, the severity of a condition, nature of the composition, and the route of administration. For example, one skilled in the art can begin with a low dosage that can be increased until reaching the desired treatment outcome or result. Alternatively, one skilled in the art can begin with a high dosage that can be decreased until reaching a minimum dosage needed to achieve the desired treatment outcome or result. Exemplary suitable dosages of inosine and the related compounds may include from about 0.5 g to about 5 g per day in humans. In a further embodiment, an individual may be administered inosine in combination with ICB in a dosage of inosine about 50-100 mg/kg per day in humans. Exemplary suitable dosages of isoprinosine may include from about 0.5 g to about 5 g per day in humans. One exemplary suitable dosage of PD1 inhibitors may include about 1.0 μM. In a further embodiment, an individual may be administered a PD1 inhibitor in combination with inosine or compounds in a dosage of PD1 inhibitor of about 5 mg/kg. One exemplary suitable dosage of PD-L1 inhibitors may include about 1.0 μM. In a further embodiment, an individual may be administered a PD-L1 inhibitor in combination with inosine or compounds in a dosage of PD-L1 inhibitor of about 5 mg/kg. One exemplary suitable dosage of CTLA4 inhibitors may include about 1.0 μM. In a further embodiment, an individual may be administered a CTLA4 inhibitor in combination with inosine or compounds in a dosage of a CTLA4 inhibitor of about 3 mg/kg. In a further embodiment, an individual may be administered isoprinosine in combination with ICB in a dosage of inosine about 100 mg/kg per day in a human.

For repeated administrations over several days or longer, depending on the condition, the treatment is sustained until a desired suppression of symptoms occurs or until sufficient therapeutic levels are achieved to alleviate cancer. Another exemplary dosing regimen comprises administering an initial higher dose, followed by a lower maintenance dose. However, other dosage regimens may be useful, depending on the pattern of pharmacokinetic decay that the practitioner wishes to achieve. For example, dosing from one-four times a day or a week is contemplated. In some embodiments, dosing frequency is once every day, every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the Binding Agent used) can vary over time.

Conventional methods, known to those of ordinary skill in the art of medicine, can be used to administer the pharmaceutical composition to the subject, depending upon the treatment goal and the cancer site.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like).

For intravenous injection, water soluble antibodies can be administered by the drip method, whereby a pharmaceutical formulation containing the formulation and physiologically acceptable excipients is infused. Physiologically acceptable excipients may include, for example, 5% dextrose, 0.9% saline, Ringer's solution or other suitable excipients.

Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, the formulation is administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts, and stents or other implantable devices, site specific carriers, direct injection, or direct application. See, e.g., WO 00/53211 and U.S. Pat. No. 5,981,568.

In another embodiment of the present disclosure, an article of manufacture is provided which contains any of the pharmaceutical compositions and formulations described herein (e.g., comprising a Binding Agent and inosine or a related compound) and provides instructions for its use and/or reconstitution. The article of manufacture comprises a container. Suitable containers include, for example, bottles, vials (e.g. dual chamber vials), syringes (such as dual chamber syringes) and test tubes. The container may be formed from a variety of materials such as glass or plastic. The container holds the formulation and the label on, or associated with, the container may indicate directions for reconstitution and/or use. For example, the label may indicate that the formulation is reconstituted to particular protein concentrations. The container holding the formulation may be a multi-use vial, which allows for repeat administrations (e.g., from 2-6 administrations) of the reconstituted formulation. The article of manufacture may further comprise a second container comprising a suitable diluent (e.g. BWFI). Upon mixing of the diluent and the lyophilized formulation, the final protein concentration in the reconstituted formulation will generally be at least 50 mg/mL. The article of manufacture may further include other materials desirable from a commercial and user standpoint, including other buffers, diluents, filters, needles, syringes, and package inserts with instructions for use.

Unless defined otherwise, all technical and scientific terms used herein have the same meaning as commonly understood by one of ordinary skill in the art to which the disclosure belongs.

It should be understood that the pharmaceutical compositions of the present disclosure can further include additional known therapeutic agents, drugs, modifications of the synthetic compounds into prodrugs, and the like for alleviating, mediating, preventing, and treating the diseases, disorders, and conditions described herein.

In another aspect, the present disclosure relates generally to the administration of the compositions for enhancing the tumor immunogenicity and empowering the antitumor effect. Accordingly, the compositions including the combinations of inosine (or related compounds) and ICB can be administered to individuals "in need," which term refers to an individual at risk for or having any cancer, and in particular, one or more of prostate, skin, ovarian cancer; cancers of non-lymphoid parenchymal organs including the heart, placenta, skeletal muscle, and lung; breast cancer; cancers of the head and neck including various lymphomas, such as mantle cell lymphoma, Non-Hodgkin B cell lymphoma, adenoma, squamous cell carcinoma, laryngeal carcinoma, salivary carcinoma, thymomas, and thymic carcinoma; leukemia; cancers of the retina; cancers of the esophagus; multiple myeloma; melanoma; colorectal cancer; lung cancer; cervical cancer; endometrium carcinoma; gallbladder cancer; liver cancer; thyroid follicular cancer; gastric cancer; nonsmall cell lung carcinoma; glioma; urothelial cancer; bladder cancer; prostate cancer; renal cell cancer; infiltrating ductal carcinoma; and glioblastoma multiform.

An individual in need" can be a human or a non-human primate or other mammal, including a mouse, a rat, a rabbit, a cow, a pig, and other types of research and/or companion animals known to those skilled in the art.

Various functions and advantages of these and other embodiments of the present disclosure will be more fully understood from the examples shown below. The examples are intended to illustrate the benefits of the present disclosure but do not exemplify the full scope of the disclosure.

Results and Conclusions

Figure 1A:
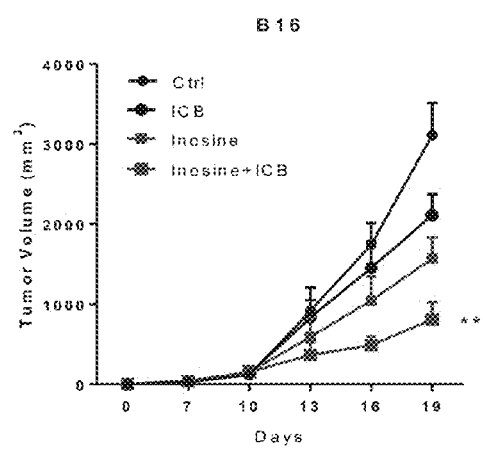
FIG. 1A shows the tumor volume (mm$^3$, y-axis) over time after B16 tumor cell challenge (x-axis) in mice treated with vehicle (Ctrl), inosine, anti-CTLA4 Ab and anti-PD-1 Ab in FIGS. 1A to 1C (labeled "ICB"; which indicates an immune checkpoint blockade/inhibitor), or inosine and ICB. B16 cells were injected subcutaneously into eight-week-old female C57BL/6 mice (2×10$^5$/mouse). Anti-CTLA4 antibody (100 μg per mouse) and anti-PD-1 antibody (200 μg per mouse) were injected i.p on days 7, 10, 13 and 16. 400 mg/kg body weight of inosine per day was orally administered to mice from day 4. It shows the enhanced tumor control observed in B16 tumor-bearing mice treated with a combination of inosine and ICB in comparison to the control group or to cohorts treated with inosine or ICB alone (wherein ** indicates P<0.01).
Figure 1B:
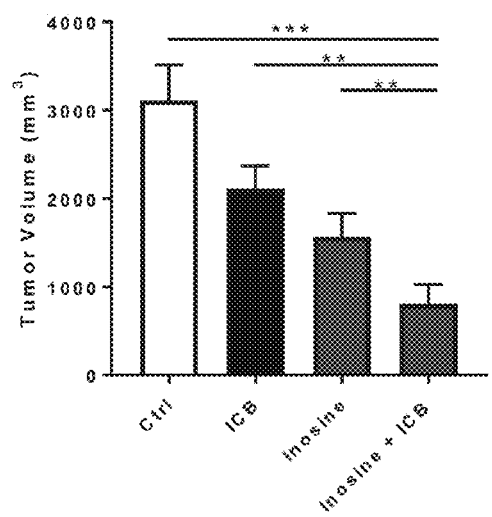
FIG. 1B shows the average tumor volumes (mm$^3$) on day 19 after B16 tumor cell challenge in mice with the treatment in FIG. 1A. Tumor volume results indicate that the combination of inosine and ICB is a better treatment than inosine or ICB alone (wherein  indicates P<0.01; * indicates P<0.001).
Figure 1C:
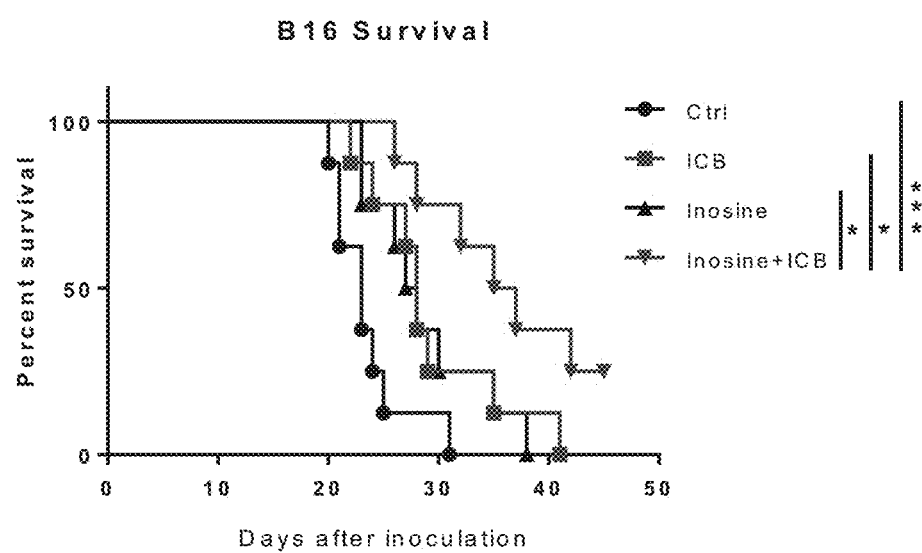
FIG. 1C shows the percent survival of B16 tumor-bearing animals that were treated with vehicle, treated with inosine, treated with ICB, or treated with inosine and ICB. Survival was defined as mice with tumors <2,500 cm$^3$. Results show that the combination of inosine and ICB treatment significantly prolongs the survival of B16 tumor-bearing mice compared with inosine or ICB treatment alone. Survival statistics calculated using Log-rank (Mantel-Cox) test (wherein * P<0.05; *** P<0.001).
Figure 2A:
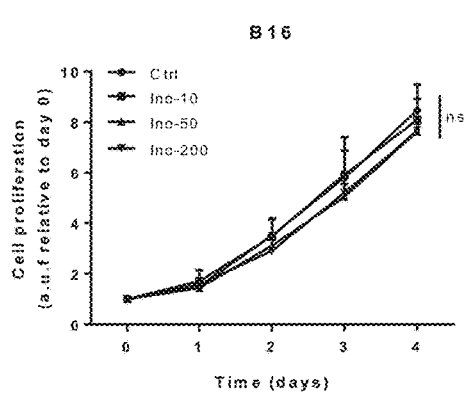
FIG. 2A shows the proliferation kinetics of B16 tumor cells using a control vehicle or inosine treatment. MTT assays were used to determine the cell viability of B16 tumor cells treated with control vehicle; the concentration of inosine administered is indicated, where "Ino-10" means 10 μM Inosine; "Ino-50" means 50 μM Inosine and "Ino-200" means 200 μM Inosine. The data demonstrate that inosine doesn't inhibit the proliferation of B16 tumor cells in vitro.
Figure 2B:
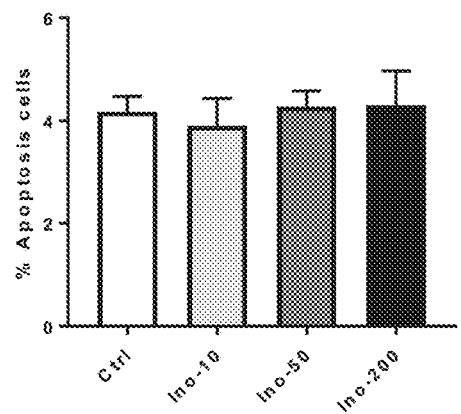
FIG. 2B shows the quantitative flow analysis in vitro of apoptotic tumor cells dosed with control vehicle or inosine (at the same concentrations as in FIG. 2A). The data indicate that inosine alone doesn't induce the apoptosis of B16 tumor cells in vitro.
Figure 2C:
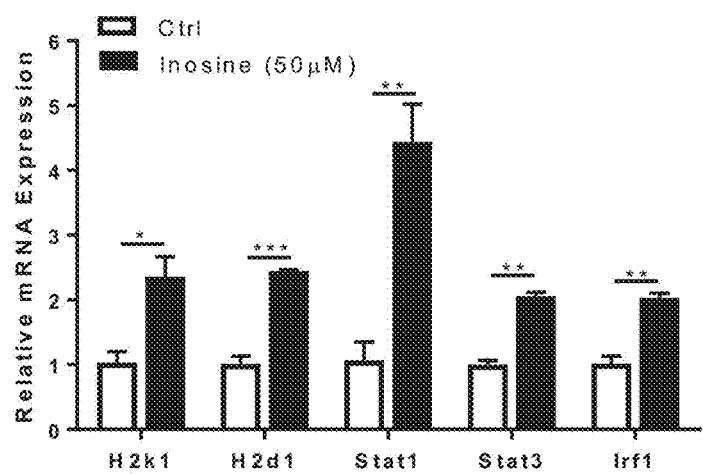
FIG. 2C shows the relative mRNA expression of antigen presentation-related genes (H2k1, H2d1) and IFN signaling genes (Stat1, Stat3, Irf1) in B16 cells treated with control or with inosine at 500. The data indicate that inosine treatment increases the expression of antigen presentation-related genes and IFN signaling genes in B16 tumor cells.
Figure 2D:
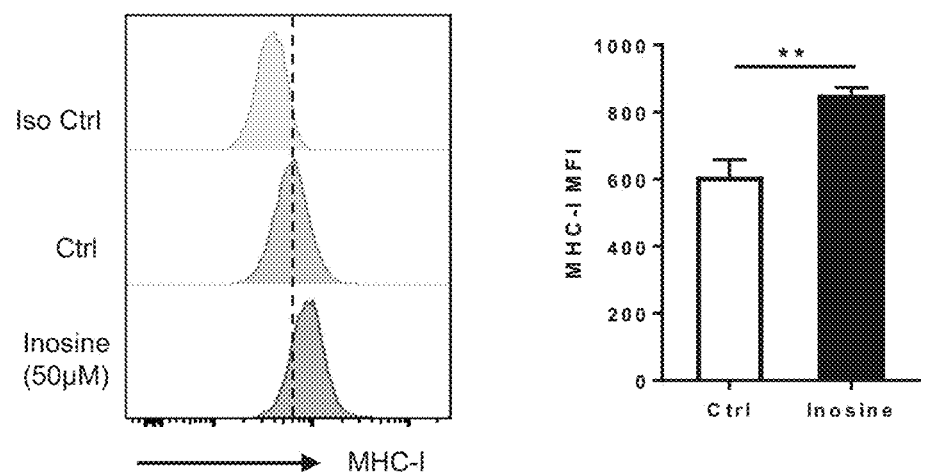
FIG. 2D shows the MHC-I (H2kb) expression in B16 with control or with inosine treatment at 500. B16 cells were stained for flow cytometry to determine the membrane MHC-I expression level. Results demonstrate that inosine treatment increases the membrane protein level of MHC-I in B16 tumor cells.
Figure 3A:
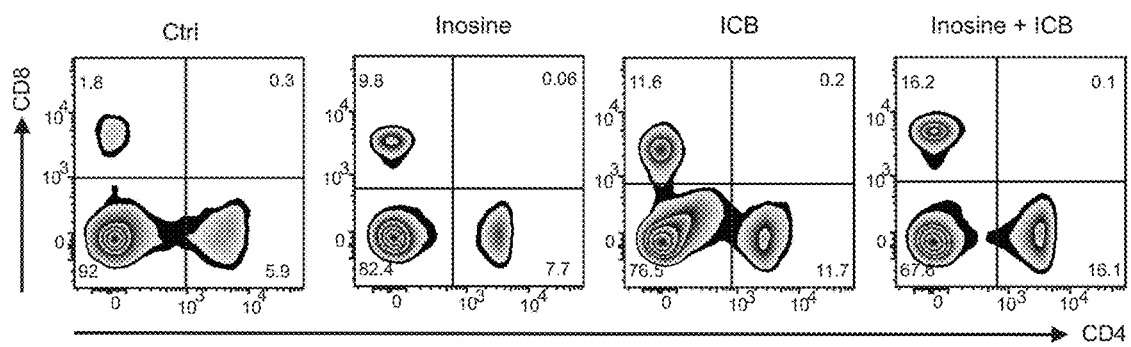
FIG. 3A shows the representative flow cytometric analysis of CD8$^+$ and CD4$^+$ T cell populations in B16 tumors with an indicated treatment at 15 days post-implantation (n=5). Tumors from the indicated treatment group were mechanically minced for the isolation of infiltrating lymphocytes. Cells were counted and stained for flow cytometry to determine the percentage of CD4$^+$ and CD8$^+$ T lymphocytes in total CD45$^+$ immune cells. The results demonstrate that the combination treatment of inosine and anti-CTLA4 antibody and anti-PD1 antibody ("ICB") increases more CD4$^+$ and CD8$^+$ T cells infiltration into tumors than either inosine or ICB treatment, alone.
Figure 3B:
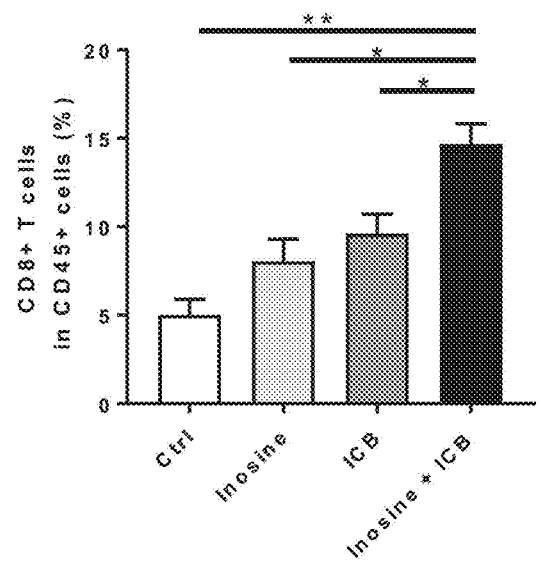
FIG. 3B shows the quantitative flow analysis of CD8$^+$ T cell population in B16 tumors treated with Ctrl (vehicle), inosine, ICB (anti-CTLA4 Ab and anti-PD-1 Ab), or inosine and ICB. This data indicates a significant increase in the presence of CD8$^+$ cytotoxic T cells in the combination cohort, as compared to the control or ICB or inosine alone (n=5 tumors). Results are shown as mean±SEM (* P<0.05; ** P<0.01) and statistics were calculated using the unpaired t-test with Welch's correction.

The effects of inosine with or without ICB on tumor growth in mice bearing B16 tumors (which is sensitive to immunotherapy) were evaluated. ICB inhibited tumor growth in mice bearing B16 tumors, suggesting this mouse model is sensitive to ICB treatment (FIG. 1A). Inosine not only inhibited tumor growth in vivo but also enhanced the antitumor efficacy of ICB and prolonged the survival of mice bearing B16 tumors (FIG. 1B, C). However, inosine didn't inhibit tumor cell proliferation and promote apoptosis in vitro, meaning that inosine has no direct effect on tumor cells. This indicates that the efficacy of inosine in vivo is not dependent on its direct effect on tumor cells (FIG. 2A, B). It was also found that inosine stimulates interferon signaling and antigen presentation-related genes in tumor cells (FIG. 2C), and hence enhances the expression of MHC-I on tumor cells (FIG. 2D). Tumor cells presenting antigen via MHC class I can be recognized by cytotoxic T lymphocytes (CTLs). Furthermore, inosine increased the cytotoxic $CD8^+$ T infiltration into tumors (FIG. 3A, B). Altogether, these findings reveal that inosine not only has antitumor effects but also enhances the antitumor effects of ICB in mice bearing B16 tumors.

To determine whether inosine overcomes the well-known resistance to immunotherapy, inosine was used with or without ICB to treat mice bearing B16-GM tumors, which is a metastatic tumor model with known resistance to immunotherapy. Inosine reduced tumor size but ICB did not significantly change the tumor growth in mice bearing B16-GM tumors (FIG. 4A, B). The combination of inosine and ICB treatment dramatically reduces the tumor growth in mice bearing B16-GM tumors (FIG. 4A, B, C, D). These results demonstrate that Inosine+ICB treatment is more efficacious than inosine or ICB treatment, alone. Notably, two of the five tumors' growth was completely inhibited by Inosine+ICB treatment (FIG. 5). Interestingly, inosine combined with ICB not only completely inhibited tumor growth but also reduced tumor metastasis (FIG. 6A, B). A significant reduction in lung metastasis was observed after inosine and inosine+ICB treatment (FIG. 6A, B). Inosine+ICB combination treatment prolonged the survival of mice bearing B16-GM tumors compared to single product treatment (FIG. 7). Collectedly, these findings demonstrate that inosine overcomes the resistance to ICB in mice with bearing B16-GM tumors.

To further test whether inosine was sufficient to overcome the resistance to immunotherapy, inosine was used with or without ICB to treat mice bearing 4T1 breast cancer cells, which are resistant to immunotherapy. ICB alone did not reduce tumor size in such 4T1 mice (FIG. 8A, B), suggesting this mouse model is resistant to the checkpoint blockade. Notably, inosine combined with ICB completely inhibited tumor growth and reduced tumor weight (FIG. 8C, D). These results demonstrate that Inosine+ICB treatment for 4T1 tumors is more efficacious than inosine or ICB treatment, alone. Notably, the growth of three of six tumors (50%) was completely inhibited by inosine+ICB treatment (FIG. 9). Altogether, these results indicate that inosine overcomes the resistance to ICB in mice bearing a 4T1 tumor. Next, we investigated the effect of other suitable compounds with a similar structure or component of inosine. Isoprinosine contains an active substance called inosine acedoben dimepranol. It is a combination of the p-acetamidobenzoate salt of N,N-dimethylamino-2-propanol and inosine in a 3:1 molar ratio. Similarly, 4T1 tumor-bearing mice were treated with vehicle, isoprinosine alone, ICB (anti-CTLA4 and anti-PD1 Ab), or the combination of isoprinosine and ICB (FIG. 10). The results demonstrated that a potent synergistic effect of the combination of isoprinosine and ICB on 4T1 tumor growth (FIG. 10A, 10B, 10C). This indicated that isoprinosine, like inosine, cooperated with immune checkpoint blockade immunotherapy.

In summary, three pre-clinical mouse model systems were employed and collectively demonstrated that inosine overcomes the resistance to ICB in different mice models. New combination strategies using inosine or inosine derivatives overcome resistance to ICB immunotherapy.

METHODS AND MATERIALS

Cell Lines

The B16-F0 murine melanoma carcinoma cell line (referred as to B16), B16-F10 and 4T1 murine breast cancer cell line (4T1) was obtained from the American Type Culture Collection (National Cancer Institute). B16-F10 cells secreting GM-CSF (referred as to B16-GM) were generated by retroviral-mediated gene transfer, as previously described. GM-CSF secretion was approximately 150 ng/$10^6$ cells per 24 hours, as determined by enzyme-linked immunosorbent assay (ELISA; BD). B16-GM cell line was used as an immunogenic tumor model increasing the number of dendritic cells to the tumor eliciting systemic antitumor immunity. All the cell lines were confirmed to be *mycoplasma* free. Cells were cultured using DMEM (Corning) with 10% fetal bovine serum (Corning) and 1% Pen/Strep (Life Technologies). Cells were incubated in an incubator maintained at 37° C. and 5% $CO_2$. 75-80% of confluent cells were harvested for orthotopic injection. Anti-CTLA4 antibody (clone 9H10) and anti-PD-1 antibody (clone RPM1-14) were purchased from BioXCell (West Lebanon, N.H., USA).

Tumor Models

For the melanoma model, $2\times10^5$ B16 or B16-GM cells were harvested for orthotopic injection into the subcutaneous (s.c.) of C57BL/6J mice (6-8 weeks) using 0.25% Trypsin (Corning) and suspended in DPBS (Gibco). For the breast cancer model, $2\times10^5$ 4T1 cells were harvested for orthotopic injection into the mammary fat pad of Balb/c mice (6-8 weeks) using 0.25% Trypsin (Corning) and suspended in a 1:1 ratio of MATRIGEL (Corning) and DPBS (Gibco).

Treatment Experiments

Treatments were given as single agents or in combination with the following regimen. Inosine (Sigma-Aldrich) was dissolved in sterilized water to yield a concentration of 40 mg/ml, and administered by oral gavage once a day at 400 mg/kg body weight. Treatment was initiated on day 4 and ended on day 21 post tumor implant. Control groups received vehicle (water) by oral gavage. Anti-CTLA4 antibody (100 μg per mouse, clone 9H10, BioXCell, West Lebanon N.H.) and anti-PD-1 antibody (200 μg per mouse, clone RPM1-14, BioXCell, West Lebanon N.H.) were injected intraperitoneally (i.p.) on days 7, 10, 13 and 16 for the treatment group. Control groups received isotype control antibody (clone LTF-2) intraperitoneally (i.p.). Tumors were measured every third day with a caliper, and measurements were assessed manually by assessing the longest dimension (length) and the longest perpendicular dimension (width). Tumor volume was estimated with the formula: $(L\times W^2)/2$.

Cell Proliferation Assays

Cell proliferation ability was examined at 0, 24, 48, 72 h and 96 h using a Cell Proliferation Reagent Kit I (MTT; Sigma) according to the manufacturer's instruction. Cells were seeded in a 96-well plate in triplicate at a concentration of $2\times10^3$ cells/well. On the indicated day, the medium was removed and the MTT solution was added to the wells. Four hours later, DMSO was added and the cells were further incubated for 10 min with gentle shaking at 37° C. Finally, the optical density of each well was measured using a microplate reader at 550 nm.

Cell Apoptosis Assays

Tumor cells were seeded in a 6-well plate and grown for 24 h. Cells were then treated with control (vehicle) or 1, 10, 50, 100 μM inosine. After 48 h of treatment, cells were harvested by trypsinization, resuspended at $10^6$ cells/ml in 1× Annexin V Binding Buffer (BD Biosciences), and 100 μl ($10^5$ cells) were added to each FACS tube. Cells were stained with 7-AAD (5 μl/100 μl, BD Biosciences, to assess cell death), and APC-conjugated Annexin V (5 μl/100 μl, BD Biosciences, to assess apoptosis) for 30 min and analyzed by BD FACSCanto II. FACS data were acquired using FACSDiva (BD Biosciences) and analyzed using FlowJo software (Tree Star) and the percentage of $APC^+$ cells obtained.

Reverse Transcription Quantitative PCR

Tumor cells cDNA was prepared using 1 µg RNA with the qScript cDNA Synthesis Kit (Bio-Rad). SYBR green-based qPCR was performed using murine primers to H2k1, H2d1, Stat1, Stat3, and Irf1. Relative copy number was determined by calculating the fold-change difference in the gene of interest relative to 18sRNA ($\Delta Ct=Ct$ gene of interest$-C_t$ 18sRNA) and reported as relative mRNA expression ($\Delta\Delta C_t = 2^{-(\Delta Ct\ sample - \Delta Ct\ control)}$) or fold change. qPCR was performed on an Applied Biosystems 7300 machine.

Flow Cytometry

For MHC-I expression flow analysis on the tumor cell, one million cells per condition were stained with the PE anti-mouse H-2Kb antibody (Biolegend) diluted in PBS plus 2% FBS and kept for 30 min on ice. Matched isotype control Ab was performed as a control.

Mouse tumor samples were minced with scissors before incubation with dissociation buffer (2 mg/ml collagenase type A, 0.02 mg/ml DNase in RPMI1640 containing 5% FBS, PenStrep) with agitation at 37° C. for 45 min. Tumor samples were homogenized by repeated pipetting and filtered through a 70-µm nylon filter (BD Biosciences) in RPMI supplemented with 10% FBS to generate single-cell suspensions. Cell suspensions were washed once with complete RPMI. After lysis of red blood cells, single-cell suspensions were blocked with anti-CD16/32 (Biolegend) for 20 min on ice and then incubated with appropriate antibodies for 30 min on ice: anti-CD45-APC-Cy7, CD3-FITC, CD8-PercP-Cy5.5, CD4-PE. Dead cells and doublets were excluded on the basis of forward and side scatter and Fixable Viability Dye eFluor 450 (eBioscience). Flow cytometry was performed on FACSCanto II (BD Biosciences), and data were analyzed using FlowJo (TreeStar).

The specific methods, procedures, formulations, antibodies, proteins, and compounds described herein are representative of preferred embodiments and are exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

REFERENCES

Ansell, S. M., Lesokhin, A. M., Borrello, I., Halwani, A., Scott, E. C., Gutierrez, M., Schuster, S. J., Millenson, M. M., Cattry, D., Freeman, G. J., et al. (2015). PD-1 blockade with nivolumab in relapsed or refractory Hodgkin's lymphoma. The New England journal of medicine 372, 311-319.

Carbone, D. P., Reck, M., Paz-Ares, L., Creelan, B., Horn, L., Steins, M., Felip, E., van den Heuvel, M. M., Ciuleanu, T. E., Badin, F., et al. (2017). First-Line Nivolumab in Stage IV or Recurrent Non-Small-Cell Lung Cancer. The New England journal of medicine 376, 2415-2426.

George, S., Rini, B. I., and Hammers, H. J. (2018). Emerging Role of Combination Immunotherapy in the First-line Treatment of Advanced Renal Cell Carcinoma: A Review. JAMA oncology.

Hasko, G., Sitkovsky, M. V., and Szabo, C. (2004). Immunomodulatory and neuroprotective effects of inosine. Trends Pharmacol Sci 25, 152-157.

Migden, M. R., Rischin, D., Schmults, C. D., Guminski, A., Hauschild, A., Lewis, K. D., Chung, C. H., Hernandez-Aya, L., Lim, A. M., Chang, A. L. S., et al. (2018). PD-1 Blockade with Cemiplimab in Advanced Cutaneous Squamous-Cell Carcinoma. The New England journal of medicine 379, 341-351.

Motzer, R. J., Tannir, N. M., McDermott, D. F., Aren Frontera, O., Melichar, B., Choueiri, T. K., Plimack, E. R., Barthelemy, P., Porta, C., George, S., et al. (2018). Nivolumab plus Ipilimumab versus Sunitinib in Advanced Renal-Cell Carcinoma. The New England journal of medicine 378, 1277-1290.

Pitt, J. M., Vetizou, M., Daillere, R., Roberti, M. P., Yamazaki, T., Routy, B., Lepage, P., Boneca, I. G., Chamaillard, M., Kroemer, G., and Zitvogel, L. (2016). Resistance Mechanisms to Immune-Checkpoint Blockade in Cancer: Tumor-Intrinsic and -Extrinsic Factors. Immunity 44, 1255-1269.

Sharma, P., Hu-Lieskovan, S., Wargo, J. A., and Ribas, A. (2017). Primary, Adaptive, and Acquired Resistance to Cancer Immunotherapy. Cell 168, 707-723.

Tawbi, H. A., Forsyth, P. A., Algazi, A., Hamid, O., Hodi, F. S., Moschos, S. J., Khushalani, N. I., Lewis, K., Lao, C. D., Postow, M. A., et al. (2018). Combined Nivolumab and Ipilimumab in Melanoma Metastatic to the Brain. The New England journal of medicine 379, 722-730.

Welihinda, A. A., Kaur, M., Greene, K., Zhai, Y., and Amento, E. P. (2016). The adenosine metabolite inosine is a functional agonist of the adenosine A2A receptor with a unique signaling bias. Cell Signal 28, 552-560.

What is claimed is:

1. A method of treating tumors or cancers by enhancing anti-tumor immunity by administering a formulation consisting essentially of inosine or a related compound and an immune checkpoint blockade binding agent to a subject in need of treatment.

2. The method of claim 1 wherein the related compounds include hypoxanthine, xanthine, hydroxyl-deoxyguanosine, 2',3'-Dideoxyinosin, 2'-Deoxyinosine, inosinic acid, inosine diphosphate, inosine triphosphate, sodium inosinate, isoprinosine deoxyinosine, 3'-Deoxy-3'-fluoroinosine, 1-Methylinosine, Inosine 5'-methyl monophosphate, and inosine-3',5'-Cyclic Monophosphate.

3. The method of claim 1 wherein the related compounds include:

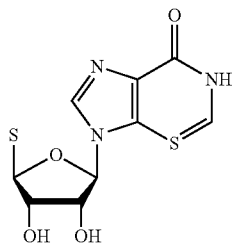

where R is an alcohol having a chain which is an alkane, alkene or alkyne, branched or unbranched, with two or more carbon atoms.

4. The method of claim 1 wherein the immune checkpoint blockade binding agent is anti-CTLA4, anti-PD1, anti-PD-L1, anti-LAG-3, anti-TIM-3, anti-TIGIT, anti-CD47 or an anti-VISTA antibody.

5. The method of claim 1 wherein the subject has a solid tumor or a hematological cancer which is one or more of: melanoma, breast cancer, lung cancer, colorectal cancer, liver cancer, gastric cancer, esophageal cancer, pancreatic cancer, head and neck cancer, ovary cancer, cervical cancer, urothelial cancer, renal cell cancer, bladder cancer, prostate cancer, lymphoma and leukemia.

6. The method of claim 5 wherein the subject bears 4T1 breast cancer cells or B16 melanoma cancer cells.

7. The method of claim 1 wherein the subject's tumor or cancer cells are sensitive or resistive to immune checkpoint blockades.

8. A formulation for treating tumors or cancers that are sensitive or resistive to immune checkpoint blockades, consisting essentially of inosine or a related compound and an immune checkpoint blockade binding agent.

9. The formulation of claim 8 wherein the immune checkpoint blockade binding agent is anti-CTLA4, anti-PD1, anti-PD-L1, anti-LAG-3, anti-TIM-3, anti-TIGIT, anti-CD47 or anti-VISTA antibodies, derivatives or fragments thereof.

10. The formulation of claim 9 wherein the antibodies, derivatives or fragments thereof are human, chimeric, humanized, an F(ab)'2, an Fab, an Fv, a single domain antibody, a bispecific antibody, a helix-stabilized antibody, a single-chain antibody molecule, a disulfide stabilized antibody, or a domain antibody.

11. The formulation of claim 8 wherein the related compounds include hypoxanthine, xanthine, hydroxyl-deoxyguanosine, 2',3'-Dideoxyinosin, 2'-Deoxyinosine, inosinic acid, inosine diphosphate, inosine triphosphate, sodium inosinate, isoprinosine, deoxyinosine, 3'-Deoxy-3'-fluoroinosine, 1-Methylinosine, Inosine 5'-methyl monophosphate, and inosine-3',5'-Cyclic Monophosphate.

12. The formulation of claim 8 wherein the related compounds include:

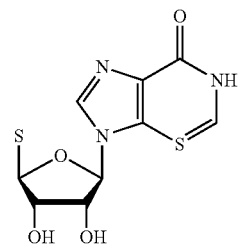

where R is an alcohol having a chain which is an alkane, alkene or alkyne, branched or unbranched, with two or more carbon atoms.

13. The formulation of claim 8 further including preservatives, diluents or antibiotics.

14. The formulation of claim 8 further including agents to make it suitable for injection or oral administration.

15. The formulation of claim 8 which is lyophilized.

16. The method of claim 4 wherein the anti-CTLA4, anti-PD1, anti-PD-L1, anti-LAG-3, anti-TIM-3, anti-TIGIT, anti-CD47 or anti-VISTA antibody is a human, chimeric, humanized, an F(ab)'2, an Fab, an Fv, a single domain antibody, a bispecific antibody, a helix-stabilized antibody, a single-chain antibody molecule, a disulfide stabilized antibody, or a domain antibody.

* * * * *